US010903521B2

(12) United States Patent
Moganty et al.

(10) Patent No.: US 10,903,521 B2
(45) Date of Patent: Jan. 26, 2021

(54) MODIFIED IONIC LIQUIDS CONTAINING TRIAZINE

(71) Applicant: NOHMs Technologies, Inc., Rochester, NY (US)

(72) Inventors: Surya Moganty, Henrietta, NY (US); Yue Wu, Rochester, NY (US); Luigi Abbate, Rochester, NY (US); Kevin Brown, Rochester, NY (US); John Sinicropi, Rochester, NY (US); Gabriel Torres, Rochester, NY (US)

(73) Assignee: NOHMS Technologies, Inc., Rochester, NY (US)

( * ) Notice: Subject to any disclaimer, the term of this patent is extended or adjusted under 35 U.S.C. 154(b) by 90 days.

(21) Appl. No.: 16/037,902

(22) Filed: Jul. 17, 2018

(65) Prior Publication Data
US 2019/0020061 A1 Jan. 17, 2019

Related U.S. Application Data

(60) Provisional application No. 62/533,410, filed on Jul. 17, 2017.

(51) Int. Cl.
H01M 10/0567 (2010.01)
H01M 10/0569 (2010.01)
H01M 10/0525 (2010.01)
H01M 4/505 (2010.01)
H01M 4/525 (2010.01)
H01M 4/587 (2010.01)
H01M 2/16 (2006.01)
C07D 251/30 (2006.01)
H01G 11/62 (2013.01)
H01G 11/60 (2013.01)
H01G 11/64 (2013.01)
H01G 11/46 (2013.01)
H01G 11/06 (2013.01)
H01G 11/52 (2013.01)
H01G 9/20 (2006.01)
H01M 10/0568 (2010.01)
H01M 6/16 (2006.01)
H01M 10/054 (2010.01)

(52) U.S. Cl.
CPC ...... H01M 10/0567 (2013.01); C07D 251/30 (2013.01); H01G 9/2013 (2013.01); H01G 9/2036 (2013.01); H01G 11/06 (2013.01); H01G 11/46 (2013.01); H01G 11/52 (2013.01); H01G 11/60 (2013.01); H01G 11/62 (2013.01); H01G 11/64 (2013.01); H01M 2/1653 (2013.01); H01M 4/505 (2013.01); H01M 4/525 (2013.01); H01M 4/587 (2013.01); H01M 6/168 (2013.01); H01M 10/054 (2013.01); H01M 10/0525 (2013.01); H01M 10/0568 (2013.01); H01M 10/0569 (2013.01); H01M 2300/0037 (2013.01); H01M 2300/0045 (2013.01)

(58) Field of Classification Search
CPC .. C07D 251/30; H01G 9/2013; H01G 9/2036; H01G 11/06; H01G 11/46; H01G 11/52; H01G 11/60; H01G 11/62; H01G 11/64; H01M 2/1653; H01M 4/505; H01M 4/525; H01M 4/587; H01M 6/168; H01M 10/0525; H01M 10/054; H01M 10/0567; H01M 10/0568; H01M 10/0569; H01M 2300/0037; H01M 2300/0043
See application file for complete search history.

(56) References Cited

U.S. PATENT DOCUMENTS

| | | | |
|---|---|---|---|
| 2002/0012836 A1* | 1/2002 | Segawa | H01M 2/0413 429/174 |
| 2006/0091010 A1* | 5/2006 | Komatsu | G01N 27/4074 204/427 |
| 2007/0020519 A1 | 1/2007 | Kim et al. | |
| 2008/0008938 A1* | 1/2008 | Wu | C01B 25/45 429/221 |
| 2009/0166615 A1* | 7/2009 | Nakata | H01L 51/005 257/40 |
| 2010/0266902 A1* | 10/2010 | Takano | B82Y 30/00 429/231.95 |
| 2012/0135286 A1* | 5/2012 | Han | H01M 2/14 429/94 |
| 2013/0149602 A1* | 6/2013 | Luski | H01M 4/0459 429/188 |
| 2015/0140446 A1* | 5/2015 | Li | H01M 10/0567 429/332 |
| 2015/0364794 A1 | 12/2015 | Nakazawa et al. | |
| 2017/0040642 A1 | 2/2017 | Ito et al. | |

OTHER PUBLICATIONS

Omotowa, B.A., Shreeve, J.M.—Triazine-Based Polyfluorinated Triquaternary Liquid Salts: Synthesis, Characterization, and Application as Solvents in Rhodium(I)-Catalyzed Hydroformilation of 1-Octene, Organometallics, 2004, 23, pp. 783-791 (Year: 2004).*
Li, H.-Y., Chu, Y.-H.—Reaction-Based Amine and Alcohol Gases Detection with Triazine Ionic Liquid Materials, Molecules, 2020, 25, 104 (Year: 2020).*
Shafiee, M., Khosropour, A.R., Mohammadpoor—Baltork, I., Moghadam, M., Tangestaninejad, S., Mirkhani, V.—A new green catalyst: 1,3,5-triazine-functionalized bisimidazolium dichloride tethered SPION catalyzed Betty synthesis, Catalysis Science& Techonolgy, 2012, 2, pp. 2440-2444 (Year: 2012).*

(Continued)

Primary Examiner — Anca Eoff
(74) Attorney, Agent, or Firm — Bond, Schoeneck & King, PLLC; Joseph Noto

(57) ABSTRACT

The present disclosure is directed to a triazine-modified ionic liquid compound, the synthesis thereof and an electrochemical cell electrolyte containing the triazine-modified ionic liquid compound.

24 Claims, 1 Drawing Sheet

(56) References Cited

OTHER PUBLICATIONS

Seijas, J.A., Vazquez-Tato, M.P.—Tris-imidazolium derivatives of isocyanuric acid. A lead for tripodal ionic liquids and anion receptors, International Electronic Conference on Synthetic Organic Chemistry, Nov. 2013, conference computer optical disk (Year: 2013).*
PCT International Search Report, Form PCT/ISA/210, International application No. PCT/US18/042514, International filing date Jul. 17, 2018, dated Sep. 27, 2018.

* cited by examiner

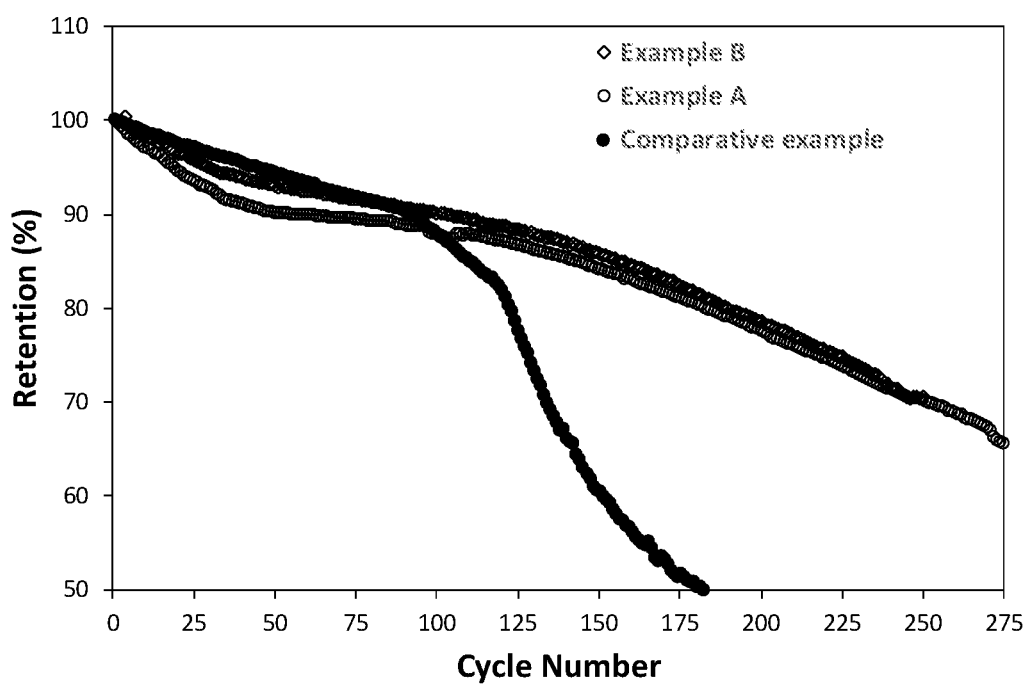

MODIFIED IONIC LIQUIDS CONTAINING TRIAZINE

CROSS REFERENCE

This application claims the benefit of the filing date of U.S. Provisional Patent Application Ser. No. 62/533,410, filed Jul. 17, 2017, which is hereby incorporated by reference in its entirety.

FIELD

This disclosure is directed towards an ionic liquid having a cation which includes a triazine moiety, an electrolyte for electrochemical cells containing the ionic liquid, and an electrochemical device containing the electrolyte.

BACKGROUND

Recent progress in synthesis and electrochemical analysis of room temperature ionic liquids (ILs) has established the promise of this unique class of materials as electrolytes for next-generation lithium-ion batteries. ILs are organic salts having melting points below 100° C. and generally consist of a bulky cation and an inorganic anion. The large cation size allows for delocalization and screening of charges, resulting in a reduction in the lattice energy and thereby the melting point or glass transition temperature. ILs have unique physicochemical properties, such as negligible vapor pressure, non-flammability, good room-temperature ionic conductivity, a wide electrochemical window, and favorable chemical and thermal stability. These properties are desirable for providing IL-based electrolytes for lithium batteries.

However, there are still safety challenges such as flammability of lithium-ion batteries under abuse conditions or even normal conditions. U.S. Pat. No. 8,697,291 to Zhang et al. teaches the use of an electrolyte composition containing a triazine-based additive, but mentions no use of an ionic liquid. Therefore, there is a need to incorporate a novel ionic liquid with flame retardant capabilities into lithium ion batteries.

SUMMARY

The present disclosure is directed towards an ionic liquid, including anions and cations, wherein the cations have at least one triazine moiety.

In accordance with one aspect of the present disclosure, there is provided an electrolyte for use in an electrical storage device, the electrolyte includes an aprotic organic solvent, an alkali metal salt, an additive and an ionic liquid compound that contains at least one triazine moiety.

In accordance with another aspect of the present disclosure, there is provided an electrolyte in an electrical energy storage device, the electrolyte includes an aprotic organic solvent, an alkali metal salt, an additive and an ionic liquid compound that contains at least one triazine moiety, wherein the organic solvent is open-chain or cyclic carbonates, carboxylic acid esters, nitrites, ethers, sulfones, sulfoxides, ketones, lactones, dioxolanes, glymes, crown ethers, siloxanes, phosphoric acid esters, such as phosphates, phosphites, mono- or polyphosphazenes or mixtures thereof.

In accordance with another aspect of the present disclosure, there is provided an electrolyte in an electrical energy storage device, the electrolyte includes an aprotic organic solvent, an alkali metal salt, an additive and the ionic liquid compound that contains at least one triazine moiety, wherein the cation of the alkali metal salt is lithium, sodium, aluminum or magnesium.

In accordance with another aspect of the present disclosure, there is provided an electrolyte in an electrical energy storage device, the electrolyte including an aprotic organic solvent, an alkali metal salt, an additive and an ionic liquid compound that contains at least one triazine moiety, wherein the additive contains sulfur-containing compounds, phosphorus-containing compounds, boron-containing compounds, silicon-containing compounds, compounds containing at least one unsaturated carbon-carbon bond, carboxylic acid anhydrides or mixtures thereof.

These and others aspects of the present disclosure will become apparent upon a review of the following detailed description and the claims appended thereto.

BRIEF DESCRIPTION OF THE DRAWINGS

The FIGURE is a room temperature cycle life comparison between a Comparative Example electrolyte and electrolytes including a modified phosphate (Electrolyte 2 & 3).

DETAILED DESCRIPTION

The present disclosure is directed towards an ionic liquid compound including at least one cation and at least one anion, wherein the at least one cation is covalently bonded to at least one triazine moiety.

In an embodiment, an electrical energy storage device electrolyte includes a) an aprotic organic solvent system; b) an alkali metal salt; c) an additive; and d) an ionic liquid compound including at least one cation and an at least one anion, wherein at least one cation is covalently bonded to at least one triazine moiety.

In an embodiment, an ionic liquid compound includes an anion; and a cation attached to a triazine moiety according to the formulas:

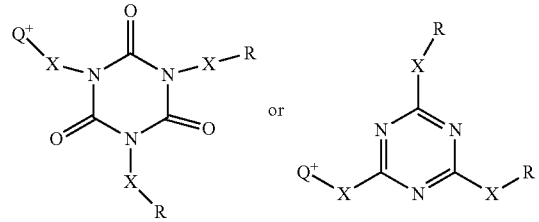

wherein: R is a $Q^+$ or $R_1$ or $R_2$; $Q^+$ is a pyrrolidinium, piperdinium, azepanium, onium, such as sulfonium and phosphonium, imidazolium, pyridine or a 5- or 6-membered heterocyclic ring having 1 to 3 heteroatoms as ring members including nitrogen, oxygen, silicon or sulfur; $R_1$ and $R_2$ are independently a $C_1$-$C_8$ alkyl, alkenyl, alkoxy, aryl, alkynyl, alkylsiloxy, phenyl, benzyl, silyl, thioether, sulfoxide, azo, amino or silane group, wherein any of the carbon or hydrogen atoms therein are optionally further substituted with a halide, alkyl, alkenyl, alkoxy, aryl, alkynyl, alkylsiloxy, phenyl, benzyl, silyl, thioether, sulfoxide, azo, amino or silane; and X is (a) a linker, including a $C_1$-$C_8$ alkylene, alkenylene, alkynylene, alkyleneoxy, ester, carbonyl, phenylene, thioether, sulfoxide, azo or arylene group, wherein any of the carbon or hydrogen atoms therein are optionally further substituted with a halide; (b) O, S or (c) O, S attached to the linker. In an embodiment the triazine-modified ionic liquid compound is present in an amount of from about 0.01 wt. % to about 50 wt. %.

Suitable anions in accordance with the present disclosure, include but are not limited to halides (e.g., Cl, Br), nitrates (e.g., $NO_3$), phosphates (e.g., $PF_6$, TFOP), imides (e.g., TFSI, BETI), borates (e.g., BOB, $BF_4$), aluminates, arsenides, cyanides, thiocyanates, nitrites, benzoates, carbonates, chlorates, chlorites, chromates, sulfates, sulfites, silicates, thiosulfates, chalcogenides, pnictogenides, crystallogenides, oxalates, acetates, formates, or hydroxides.

In the present disclosure, an electrolyte includes a thermally stable ionic liquid, an alkali metal, such as lithium, an additive and an aprotic solvent for use in an electrochemical cell. The ionic liquid contains an organic cation and an inorganic/organic anion, with the organic cation being N-alkyl-N-alkyl-pyrrolidinium, N-alkyl-N-alkyl-pyridnium, N-alkyl-N-alkyl-sulfonium, N-alkyl-N-alkyl-ammonium, N-alkyl-N-alkyl-piperdinium or the like, and the anion being tetrafluoroborate, hexafluorophosphate, bis(trifluoromethylsulfonyl)imide, lithium bis(fluorosulfonyl)imide, bis(pentafluoroethylsulfonyl)imide, trifluoroacetate or the like. The polymer in the electrolyte includes poly(ethylene glycol) derivatives, with varying molecular weights ranging from about 150 g/mol to about 10,000,000 g/mol. Suitable aprotic solvents include carbonates, ethers, acetamides, acetonitrile, symmetric sulfones, 1,3-dioxolanes, dimethoxyethanes, glymes, siloxanes and their blends. The alkali metal salt can be $LiBF_4$, $LiNO_3$, $LiPF_6$, $LiAsF_6$, lithium bis(trifluoromethylsulfonyl)imide (LiTFSI), lithium bis(fluorosulfonyl)imide (LiFSI), lithium bis(pentafluoroethylsulfonyl)imide, lithium trifluoroacetate, or a similar compound.

In an embodiment, the electrolyte includes a lithium salt in addition to the ionic liquid. A variety of lithium salts may be used, including, for example, $Li[CF_3CO_2]$; $Li[C_2F_5CO_2]$; $Li[ClO_4]$; $Li[BF_4]$; $Li[AsF_6]$; $Li[PF_6]$; $Li[PF_2(C_2O_4)_2]$; $Li[PF_4C_2O_4]$; $Li[CF_3SO_3]$; $Li[N(CP_3SO_2)_2]$; $Li[C(CF_3SO_2)_3]$; $Li[N(SO_2C_2F_5)_2]$; lithium alkyl fluorophosphates; $Li[B(C_2O_4)_2]$; $Li[BF_2C_2O_4]$; $Li_2[B_{12}Z_{12-j}H_j]$, $Li_2[B_{10}X_{10-j'}H_{j'}]$; or a mixture of any two or more thereof, wherein Z is independent at each occurrence a halogen, j is an integer from 0 to 12 and j' is an integer from 1 to 10.

In some applications of the present electrolyte, such as a formulation for a lithium ion battery, aprotic solvents are combined with the present ionic liquids to decrease the viscosity and increase the conductivity of the electrolyte. The most appropriate aprotic solvents lack exchangeable protons, including cyclic carbonic acid esters, linear carbonic acid esters, oligoether substituted siloxanes/silanes, cyclic ethers, chain ethers, lactone compounds, chain esters, nitrile compounds, amide compounds, sulfone compounds, siloxanes, phosphoric acid esters, such as phosphates, phosphites, mono- or polyphosphazenes and the like. These solvents may be used singly, or at least two of them in admixture. Examples of aprotic solvents or carriers for forming the electrolyte systems include but are not limited to dimethyl carbonate, ethyl methyl carbonate, diethyl carbonate, methyl propyl carbonate, ethyl propyl carbonate, dipropyl carbonate, bis(trifluoroethyl) carbonate, bis(pentafluoropropyl) carbonate, trifluoroethyl methyl carbonate, pentafluoroethyl methyl carbonate, heptafluoropropyl methyl carbonate, perfluorobutyl methyl carbonate, trifluoroethyl ethyl carbonate, pentafluoroethyl ethyl carbonate, heptafluoropropyl ethyl carbonate, perfluorobutyl ethyl carbonate, etc., fluorinated oligomers, methyl propionate, ethyl propionate, butyl propionate, dimethoxyethane, triglyme, dimethylvinylene carbonate, tetraethyleneglycol, dimethyl ether, polyethylene glycols, triphenyl phosphate, tributyl phosphate, hexafluorocyclotriphosphazene, 2-Ethoxy-2,4,4,6,6-pentafluoro-1,3,5,2-5,4-5,6-5 triazatriphosphinine, triphenyl phosphite, sulfolane, dimethyl sulfoxide, ethyl methyl sulfone, ethylvinyl sulfone, allyl methyl sulfone, divinyl sulfone, fluorophenylmethyl sulfone and gamma-butyrolactone.

In an embodiment, the electrolytes further include an additive to protect the electrodes from degradation. Thus, electrolytes of the present technology may include an additive that is reduced or polymerized on the surface of a negative electrode to form a passivation film on the surface of the negative electrode. Likewise, electrolytes can include an additive that can be oxidized or polymerized on the surface of the positive electrode to form a passivation film on the surface of the positive electrode. Furthermore, electrolyte may encompass additives acting as scavenging agents for water, acids, and undesirable metal ions. In an embodiment, electrolytes of the present technology further include mixtures of the three types of additives.

In an embodiment, an additive is a substituted or unsubstituted linear, branched or cyclic hydrocarbon including at least one oxygen atom and at least one aryl, alkenyl or alkynyl group. The passivating film formed from such additives may also be formed from a substituted aryl compound or a substituted or unsubstituted heteroaryl compound where the additive includes at least one oxygen atom.

Representative additives include glyoxal bis(diallyl acetal), tetra(ethylene glycol) divinyl ether, 1,3,5-triallyl-1,3,5-triazine-2,4,6(1H,3H,5H)-trione, 1,3,5,7-tetravinyl-1,3,5,7-tetramethylcyclotetrasiloxane, 2,4,6-triallyloxy-1,3,5-triazine, 1,3,5-triacryloylhexahydro-1,3,5-triazine, 1,2-divinyl furoate, 1,3-butadiene carbonate, 1-vinylazetidin-2-one, 1-vinylaziridin-2-one, 1-vinylpiperidin-2-one, 1 vinylpyrrolidin-2-one, 2,4-divinyl-1,3-dioxane, 2-amino-3-vinylcyclohexanone, 2-amino-3-vinylcyclopropanone, 2 amino-4-vinylcyclobutanone, 2-amino-5-vinylcyclopentanone, 2-aryloxy-cyclopropanone, 2-vinyl-[1,2]oxazetidine, 2 vinylaminocyclohexanol, 2-vinylaminocyclopropanone, 2-vinyloxetane, 2-vinyloxy-cyclopropanone, 3-(N-vinylamino)cyclohexanone, 3,5-divinyl furoate, 3-vinylazetidin-2-one, 3 vinylaziridin-2-one, 3-vinylcyclobutanone, 3-vinylcyclopentanone, 3-vinyloxaziridine, 3-vinyloxetane, 3-vinylpyrrolidin-2-one, 2-vinyl-1,3-dioxolane, acrolein diethyl acetal, acrolein dimethyl acetal, 4,4-divinyl-3-dioxolan-2-one, 4-vinyltetrahydropyran, 5-vinylpiperidin-3-one, allylglycidyl ether, butadiene monoxide, butyl-vinyl-ether, dihydropyran-3-one, divinyl butyl carbonate, divinyl carbonate, divinyl crotonate, divinyl ether, divinyl ethylene carbonate, divinyl ethylene silicate, divinyl ethylene sulfate, divinyl ethylene sulfite, divinyl methoxypyrazine, divinyl methylphosphate, divinyl propylene carbonate, ethyl phosphate, methoxy-o-terphenyl, methyl phosphate, oxetan-2-yl-vinylamine, oxiranylvinylamine, vinyl carbonate, vinyl crotonate, vinyl cyclopentanone, vinyl ethyl-2-furoate, vinyl ethylene carbonate, vinyl ethylene silicate, vinyl ethylene sulfate, vinyl ethylene sulfite, vinyl methacrylate, vinyl phosphate, vinyl-2-furoate, vinylcylopropanone, vinylethylene oxide, 3-vinyl-γ-butyrolactone or a mixture of any two or more thereof. In some embodiments, the additive may be a cyclotriphosphazene that is substituted with F, alkyloxy, alkenyloxy, aryloxy, methoxy, allyloxy groups or combinations thereof. For example, the additive may be a (divinyl)-(methoxy)(trifluoro)cyclotriphosphazene, (trivinyl)(difluoro)(methoxy)cyclotriphosphazene, (vinyl)(methoxy)(tetrafluoro)cyclotriphosphazene, (aryloxy)(tetrafluoro)(methoxy)cyclotriphosphazene or (diaryloxy)(trifluoro)(methoxy)cyclotriphosphazene compounds or a mixture of two or more such compounds. In an embodiment, the additive is vinyl ethylene carbonate, vinyl carbonate, or 1,2-diphenyl ether, or a mixture of any two or more such compounds.

Other representative additives include compounds with phenyl, naphthyl, anthracenyl, pyrrolyl, oxazolyl, furanyl, indolyl, carbazolyl, imidazolyl, thiophenyl, fluorinated carbonates, sultone, sulfide, anhydride, silane, siloxy, phosphate or phosphite groups. For example, additives may be phenyl trifluoromethyl sulfide, fluoroethylene carbonate, 1,3,2-dioxathiolane 2,2-dioxide, 1-propene 1,3-sultone, 1,3-propanesultone, 1,3-dioxolan-2-one, 4-[(2,2,2-trifluoroethoxy)methyl], 1,3-dioxolan-2-one, 4-[[2,2,2-trifluoro-1-(trifluoromethyl)ethoxy]methyl]-, methyl 2,2,2-trifluoroethyl carbonate, nonafluorohexyltriethoxysilane, octamethyltrisiloxane, methyltris(trimethylsiloxy)silane, tetrakis(trimethylsiloxy)silane, (tridecafluoro-1,1,2,2-tetrahydrooctyl)triethoxysilane, tris(1H1H-heptafluorobutyl)phosphate, 3,3,3-trifluoropropyltris(3,3,3-trifluoropropyldimethylsiloxy) silane, (3,3,3-trifluoropropyl)trimethoxysilane, trimethylsilyl trifluoromethanesulfonate, tris(trimethylsilyl) borate, tripropyl phosphate, bis(trimethylsilylmethyl)benzylamine, phenyltris(trimethylsiloxy)silane, 1,3-bis(trifluoropropyl)tetramethyldisiloxane, triphenyl phosphate, tris(trimethylsilyl)phosphate, tris(1H.1H,5H-octafluoropentyl) phosphate, triphenyl phosphite, trilauryl trithiophosphite, tris(2,4-di-tert-butylphenyl) phosphite, tri-p-tolyl phosphite, tris(2,2,3,3,3-pentafluoropropyl)phosphate, succinic anhydride, 1,5,2,4-dioxadithiane 2,2,4,4-tetraoxide, tripropyl trithiophosphate, aryloxpyrrole, aryloxy ethylene sulfate, aryloxy pyrazine, aryloxy-carbazole trivinylphosphate, aryloxy-ethyl-2-furoate, aryloxy-o-terphenyl, aryloxy-pyridazine, butyl-aryloxy-ether, divinyl diphenyl ether, (tetrahydrofuran-2-yl)-vinylamine, divinyl methoxybipyridine, methoxy-4-vinylbiphenyl, vinyl methoxy carbazole, vinyl methoxy piperidine, vinyl methoxypyrazine, vinyl methyl carbonate-allylanisole, vinyl pyridazine, 1-divinylimidazole, 3-vinyltetrahydrofuran, divinyl furan, divinyl methoxy furan, divinylpyrazine, vinyl methoxy imidazole, vinyl-methoxy pyrrole, vinyl-tetrahydrofuran, 2,4-divinyl isooxazole, 3,4 divinyl-1-methyl pyrrole, aryloxyoxetane, aryloxy-phenyl carbonate, aryloxy-piperidine, aryloxy-tetrahydrofuran, 2-aryl-cyclopropanone, 2-diaryloxy-furoate, 4-allylanisole, aryloxy-carbazole, aryloxy-2-furoate, aryloxy-crotonate, aryloxy-cyclobutane, aryloxy-cyclopentanone, aryloxy-cyclopropanone, aryloxy-cycolophosphazene, aryloxy-ethylene silicate, aryloxy-ethylene sulfate, aryloxy-ethylene sulfite, aryloxy-imidazole, aryloxy-methacrylate, aryloxy-phosphate, aryloxy-pyrrole, aryloxyquinoline, diaryloxycyclotriphosphazene, diaryloxy ethylene carbonate, diaryloxy furan, diaryloxy methyl phosphate, diaryloxy-butyl carbonate, diaryloxy-crotonate, diaryloxy-diphenyl ether, diaryloxy-ethyl silicate, diaryloxy-ethylene silicate, diaryloxy-ethylene sulfate, diaryloxyethylene sulfite, diaryloxy-phenyl carbonate, diaryloxy-propylene carbonate, diphenyl carbonate, diphenyl diaryloxy silicate, diphenyl divinyl silicate, diphenyl ether, diphenyl silicate, divinyl methoxydiphenyl ether, divinyl phenyl carbonate, methoxycarbazole, or 2,4-dimethyl-6-hydroxy-pyrimidine, vinyl methoxyquinoline, pyridazine, vinyl pyridazine, quinoline, vinyl quinoline, pyridine, vinyl pyridine, indole, vinyl indole, triethanolamine, 1,3-dimethyl butadiene, butadiene, vinyl ethylene carbonate, vinyl carbonate, imidazole, vinyl imidazole, piperidine, vinyl piperidine, pyrimidine, vinyl pyrimidine, pyrazine, vinyl pyrazine, isoquinoline, vinyl isoquinoline, quinoxaline, vinyl quinoxaline, biphenyl, 1,2-diphenyl ether, 1,2-diphenylethane, o terphenyl, N-methyl pyrrole, naphthalene or a mixture of any two or more such compounds.

In an embodiment, the electrolyte of the present technology includes an aprotic gel polymer carrier/solvent. Suitable gel polymer carrier/solvents include polyethers, polyethylene oxides, polyimides, polyphosphazines, polyacrylonitriles, polysiloxanes, polyether grafted polysiloxanes, derivatives of the foregoing, copolymers of the foregoing, cross-linked and network structures of the foregoing, blends of the foregoing and the like, to which is added a suitable ionic electrolyte salt. Other gel-polymer carrier/solvents include those prepared from polymer matrices derived from polypropylene oxides, polysiloxanes, sulfonated polyimides, perfluorinated membranes (Nafion resins), divinyl polyethylene glycols, polyethylene glycol-bis-(methyl acrylates), polyethylene glycol-bis(methyl methacrylates), derivatives of the foregoing, copolymers of the foregoing and cross-linked and network structures of the foregoing.

The electrolytic solution containing the salt are high in electrical conductivity and solubility in organic solvents and are suitable for use as an electrolytic solution for electrochemical devices. Examples of electrochemical devices are electric double-layer capacitor, secondary batteries, solar cells of the pigment sensitizer type, electrochromic devices and condensers, and this list is not limitative. Especially suitable as electrochemical devices are electric double-layer capacitor and secondary batteries, such as a lithium ion battery.

In yet another aspect, an electrochemical device is provided that includes a cathode, an anode and an electrolyte including modified ionic liquid containing triazine as described herein. In one embodiment, the electrochemical device is a lithium secondary battery. In an embodiment, the secondary battery is a lithium battery, a lithium-ion battery, a lithium-sulfur battery, a lithium-air battery, a sodium ion battery or a magnesium battery. In an embodiment, the electrochemical device is an electrochemical cell, such as a capacitor. In an embodiment, the capacitor is an asymmetric capacitor or supercapacitor. In an embodiment, the electrochemical cell is a primary cell. In an embodiment, the primary cell is a lithium/$MnO_2$ battery or Li/poly(carbon monofluoride) battery. In an embodiment, the electrochemical cell is a solar cell.

Suitable cathodes include those such as, but not limited to, a lithium metal oxide, spinel, olivine, carbon-coated olivine, $LiFePO_4$, $LiCoO_2$, $LiNiO_2$, $LiNi_xCo_yMet_zO_2$, $LiMn_{0.5}Ni_{0.5}O_2$, $LiMn_{0.3}Co_{0.3}Ni_{0.3}O_2$, $LiMn_2O_4$, $LiFeO_2$, $LiFe_{1+x}Ni_\alpha Mn_\beta Co_\gamma Met'_\delta O_{2-z}F_{z'}$, $A_nB_2(XO_4)_3$ (NASICON), vanadium oxide, lithium peroxide, sulfur, polysulfide, a lithium carbon monofluoride (also known as LiCFx) or mixtures of any two or more thereof, where Met is Al, Mg, Ti, B, Ga, Si, Mn or Co; Met' is Mg, Zn, Al, Ga, B, Zr or Ti; A is Li, Ag, Cu, Na, Mn, Fe, Co, Ni, Cu or Zn; B is Ti, V, Cr, Fe or Zr; X is P, S, Si, W or Mo; and wherein $0 \leq x \leq 0.3$, $0 \leq y \leq 0.5$, $0 \leq z \leq 0.5$, $0 \leq x' \leq 0.4$, $0 \leq \alpha \leq 1$, $0 \leq \beta \leq 1$, $0 \leq \gamma \leq 1$, $0 \leq \delta \leq 0.4$, $0 \leq z' \leq 0.4$ and $0 \leq h' \leq 3$. According to an embodiment, the spinel is a spinel manganese oxide with the formula of $Li_{1+x}Mn_{2-z}Met'''_yO_{4-m}X'_n$, wherein Met''' is Al, Mg, Ti, B, Ga, Si, Ni or Co; X' is S or F; and wherein $0 \leq x \leq 0.3$, $0 \leq y \leq 0.5$, $0 \leq z \leq 0.5$, $0 \leq m \leq 0.5$ and $0 \leq n \leq 0.5$. In an embodiment, the olivine has a formula of $Li_{1+x}Fe_{1-z}Met''_yPO_{4-m}X'_n$, wherein Met'' is Al, Mg, Ti, B, Ga, Si, Ni, Mn or Co; X' is S or F; and wherein $0 \leq x \leq 0.3$, $0 \leq y \leq 0.5$, $0 \leq z \leq 0.5$, $0 \leq m \leq 0.5$ and $0 \leq n \leq 0.5$.

Suitable anodes include those such as lithium metal, graphitic materials, amorphous carbon, $Li_4Ti_5O_{12}$, tin alloys, silicon alloys, intermetallic compounds or mixtures of any two or more such materials. Suitable graphitic materials include natural graphite, artificial graphite, graphitized meso-carbon microbeads (MCMB) and graphite fibers, as well as any amorphous carbon materials. In an embodiment, the anode and cathode are separated from each other by a porous separator.

The separator for the lithium battery often is a microporous polymer film. Examples of polymers for forming films include: nylon, cellulose, nitrocellulose, polysulfone, polyacrylonitrile, polyvinylidene fluoride, polypropylene, polyethylene, polybutene, or co-polymers or blends of any two or more such polymers. In an embodiment, the separator is an electron beam-treated micro-porous polyolefin separator. The electron treatment can improve the deformation temperature of the separator and can accordingly enhance the high temperature performance of the separator. Additionally, or alternatively, the separator can be a shut-down separator. The shut-down separator can have a trigger temperature above about 130° C. to permit the electrochemical cells to operate at temperatures up to about 130° C.

The disclosure will be further illustrated with reference to the following specific examples. It is understood that these examples are given by way of illustration and are not meant to limit the disclosure or the claims to follow.

EXAMPLES

Example 1 Ionic Liquid Synthesis of Pyr12O-DMT_TFSI

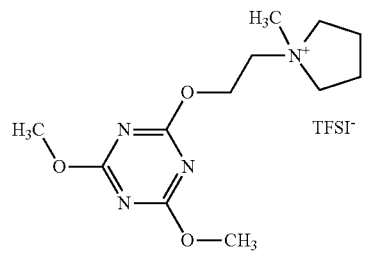

Quaternization

To a 250 mL 3-neck flask equipped with a magnetic stirring bar, water-cooled condenser, N2 inlet and thermocouple was added N-ethylpyrrolidine-4,6-dimethoxy-1,3,5-triazine in DCM (30 mL). While stirring at RT, methyliodide was added by pipet. A mild exotherm to about 34° C. was observed.

The mixture slowly returned to RT and a pale white solid precipitate gradually formed. The mixture continued to stir at RT for 6 h. The solid was collected by vacuum filtration and the mother liquor removed all the color. Yield: white solid, 2.0 g (13%).

Metathesis (TFSI)

To a 100 mL capped bottle equipped with a magnetic stirring bar were added the iodide from step 1 and lithium bis(trifluoromethylsulfonyl)imide as two separate solutions, each dissolved in 20 mL DI water. When the two solutions are combined, a cloudy precipitate quickly forms and a pale white oil deposits on the bottom. The mixture stirred at RT for 1 h.

The water layer is decanted, DCM (10 mL) is added and the entire mixture is poured into a separatory funnel. The organic layer is washed with DI water (2×10 mL), separated, dried over MgSO4 and the solvent was stripped by rotary evaporation, pumped under high vacuum and by vacuum oven (5 mbar, 60° C.). Yield: colorless oil, 2.4 g (86%). Combined batches: 11.4 g.

Characterization

FTIR: 1131, 1331, 1562 cm−1; Silver halide test: negative; Karl Fischer: 19.3 ppm;

$H^1$ NMR: (CDCl3) δ ppm 4.85 (t, 2H), 4.03 (s, 6H), 3.88 (t, 2H), 3.67 (m, 4H), 3.19 (s, 3H), 2.30 (m, 4H).

$F^{19}$ NMR: (CDCl3) δ ppm −79.02(s).

| Reagent | MW | Equiv | Mol | Mass (g) | Density | Volume (mL) | Conc | Yield (calc) |
|---|---|---|---|---|---|---|---|---|
| N-ethylPyr-4,6-dimethoxy-1,3,5-triazine | 254.24 | 1.00 | 0.040 | 10.2 | | #DIV/0! | | |
| methyliodide | 141.94 | 1.00 | 0.040 | 5.7 | 2.28 | 2.5 | | |
| DCM | | | | 53.0 | 1.326 | 40.0 | 30% | |
| Pyr12O-DMT Iodide | 396.18 | 1.00 | 0.005 | 2.0 | | | | 15.9 |
| DI water | | | | 6.3 | 1.00 | 6.3 | 80% | |
| LiTFSI | 287.09 | 1.05 | 0.005 | 3.0 | | | | |
| Pyr12O-DMT TFSI | 549.42 | | | | | | | 2.8 |

Example 2—Ionic Liquid Synthesis of PP12O-DMT_TFSI

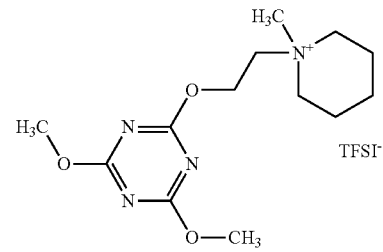

| Reagent | MW | Equiv | Mol | Mass (g) | Density | Volume (mL) | Conc | Yield (calc) |
|---|---|---|---|---|---|---|---|---|
| N-ethylPP-4,6-dimethoxy-1,3,5-triazine | 268.27 | 1.00 | 0.039 | 10.4 | | #DIV/0! | | |
| methyliodide | 141.94 | 1.00 | 0.039 | 5.5 | 2.28 | 2.4 | | |
| DCM | | | | 53.0 | 1.326 | 40.0 | 30% | |
| PP12O-4,6-DMT Iodide | 410.21 | 1.00 | 0.035 | 14.5 | | | | 15.9 |
| DI water | | | | | 1.00 | #VALUE! | 80% | |
| LiTFSI | 287.09 | 1.05 | 0.037 | 21.3 | | | | |
| PP12O-4,6-DMT TFSI | 563.45 | | | | | | | 19.9 |

Quaternization

To a 250 mL 3-neck flask equipped with a magnetic stirring bar, water-cooled condenser, N2 inlet and thermocouple was added N-ethyl piperdinium-4,6-dimethoxy-1,3,5-triazine in DCM (30 mL). While stirring at RT, methyliodide was added by pipet. A mild exotherm to about 32° C. was observed.

The mixture slowly returned to RT and a pale white solid precipitate gradually formed. The mixture continued to stir at RT for 2 h. The solid was collected by vacuum filtration and the mother liquor removed all the color. Yield: white solid, 14.5 g (92%).

H$^+$ NMR: (DMSO-d6) δ ppm 4.80 (t, 2H), 3.95 (s, 6H), 3.82 (t, 2H), 3.41 (m, 4H), 3.11 (s, 3H), 1.81 (m, 4H), 1.54 (m, 2H).

Metathesis (TFSI)

To a 100 mL capped bottle equipped with a magnetic stirring bar were added the iodide from step 1 and lithium bis(trifluoromethylsulfonyl)imide as two separate solutions, each dissolved in 50 mL DI water. When the two solutions are combined, a cloudy precipitate quickly forms and a pale white oil deposits on the bottom. The mixture stirred at RT for 1 h.

The water layer is decanted, DCM (20 mL) is added and the entire mixture is poured into a separatory funnel. The organic layer is washed with DI water (20 mL), separated, dried over MgSO4 and the solvent was stripped by rotary evaporation, pumped under high vacuum and by vacuum oven (5 mbar, 60° C.). Yield: pale amber oil, 9.4 g (47%).

Characterization

FTIR: 1130, 1334, 1562 cm−1; Silver halide test: negative;

H$^1$ NMR: (CDCl3) δ ppm 4.86 (t, 2H), 4.03 (s, 6H), 3.86 (t, 2H), 3.51 (m, 4H), 3.21 (s, 3H), 1.95 (m, 4H), 1.77 (m, 2H). F$^{19}$ NMR: (CDCl3) δ ppm −78.97(s).

TABLE A

Electrolyte formulations.

| Examples | Solvent base | Additive (1 wt %) |
|---|---|---|
| Comparative Example | 1M Li PF$_6$; EC:EMC; 3:7 w/w | NONE |
| A | 1M Li PF$_6$; EC:EMC; 3:7 w/w | 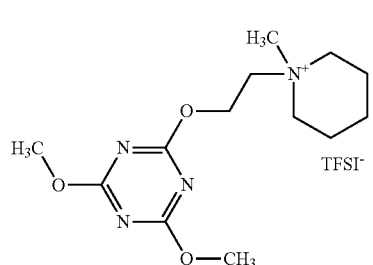 TFSI$^-$ |
| B | 1M Li PF$_6$; EC:EMC; 3:7 w/w | 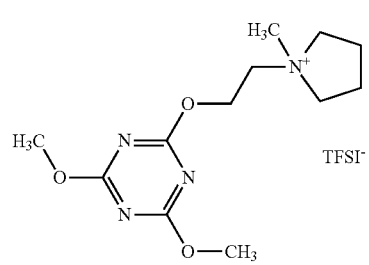 TFSI$^-$ |

Example 3

Electrolyte formulations were prepared in a dry argon filled glovebox by combining all the electrolyte components in a vial and stirring for 24 hours to ensure complete dissolution of the salts. The triazine-modified ionic liquid compound is included as an additive with a base electrolyte formulation comprising a 3:7 by weight mixture of ethylene carbonate, "EC", and ethyl methyl carbonate, "EMC", with 1 M lithium hexafluorophosphate, "LiPF6", dissolved therein.

The electrolyte formulations prepared are summarized in Table A.

Example 4

The electrolyte formulations prepared are used as the electrolyte in 200 mAh 403520 Li-ion polymer pouch cells comprising Lithium NMC622 cathode active material and graphite as the anode active material. Each electrolyte is filled in three cells. In each cell 0.9 ml of electrolyte formulation is added and allowed to soak in the cell for 1 hour prior to vacuum sealing and testing. The cells were then charged to 4.4 V and discharged to 3.0 V at a C/10 rate for formation and then by 1C discharge and charge rate cycling at room temperature. The results of this cycling test are summarized in the FIG. It is shown that electrolyte Examples A and B demonstrates capacity retention over cycle life than the comparative example electrolyte.

Although various embodiments have been depicted and described in detail herein, it will be apparent to those skilled in the relevant art that various modifications, additions, substitutions, and the like can be made without departing from the spirit of the disclosure and these are therefore considered to be within the scope of the disclosure as defined in the claims which follow.

What is claimed:

1. An ionic liquid compound, comprising:
   an anion; and
   a cation attached to a triazine moiety according to the formula:

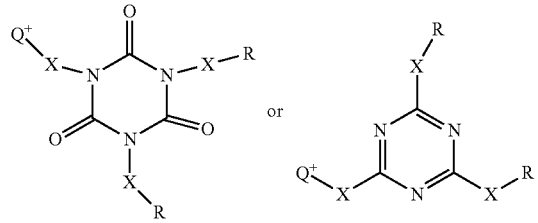

wherein:
R is a Q$^+$ or R$_1$ or R$_2$; Q$^+$ is an azepanium, sulfonium, phosphonium, or a 5- or 6-membered heterocyclic ring having 1 to 3 heteroatoms as ring members comprising nitrogen, oxygen, silicon or sulfur;
R$_1$ and R$_2$ are independently a C$_1$-C$_8$ alkyl, alkenyl, alkoxy, aryl, alkynyl, alkylsiloxy, silyl, thioether, sulfoxide, azo, silane or amino group, wherein any of the carbon or hydrogen atoms therein are optionally further substituted with a halide, alkyl, alkenyl, alkoxy, aryl, alkynyl, alkylsiloxy, silyl, thioether, sulfoxide, azo, or amino group; and
X is (a) a linker, comprising a C$_1$-C$_8$ alkylene, alkenylene, alkynylene, alkyleneoxy, ester, carbonyl, thioether, sulfoxide, azo or arylene group, wherein any of the carbon or hydrogen atoms therein are optionally further substituted with a halide; (b) O, S; or (c) O, S attached to the linker, wherein when X is O, O attached to $C_2$ alkylene or $C_2$ alkylene then $Q^+$ is not imidazolium.

2. The compound of claim 1, wherein the anion comprises a halide, aluminate, arsenide, cyanide, thiocyanate, nitrite, benzoate, chlorate, chlorite, chromate, sulfate, sulfite, silicate, thiosulfate, oxalate, acetate, formate, hydroxide, nitrate, phosphate, imide, or borate.

3. An electrical energy storage device electrolyte comprising:
   a) an aprotic organic solvent system;
   b) a metal salt;
   c) an additive; and
   d) an ionic liquid compound according to claim 1.

4. The electrolyte of claim 3, wherein the anion of either or both of the metal salt and ionic liquid comprises a halide, aluminate, arsenide, cyanide, thiocyanate, nitrite, benzoate, chlorate, chlorite, chromate, sulfate, sulfite, silicate, thiosulfate, oxalate, acetate, formate, hydroxide, nitrate, phosphate, imide, or borate.

5. The electrolyte of claim 3, wherein the aprotic organic solvent comprises an open-chain or cyclic carbonate, carboxylic acid ester, nitrite, ether, sulfone, ketone, lactone, dioxolane, glyme, crown ether, siloxane, phosphoric acid ester, phosphite, mono- or polyphosphazene or mixtures thereof.

6. The electrolyte of claim 5, wherein the phosphoric acid ester is 4-fluorophenyldiphenylphosphate, 3,5-difluorophenyldiphenylphosphate, 4-chlorophenyldiphenylphosphate, trifluorophenylphosphate, heptafluorobutyldiphenylphosphate, trifluoroethyldiphenylphosphate, bis(trifluoroethyl)phenylphosphate, or phenylbis(trifluoroethyl)phosphate.

7. The electrolyte of claim 3, wherein the additive comprises a sulfur-containing compound, phosphorus-containing compound, boron-containing compound, silicon-containing compound, fluorine-containing compound, nitrogen-containing compound, compound containing at least one unsaturated carbon-carbon bond, carboxylic acid anhydride or the mixtures thereof.

8. The electrolyte of claim 3, wherein the electrolyte comprises the ionic liquid compound in a concentration of from about 0.01 wt. % to about 50.0 wt. %.

9. An electrochemical device comprising:
   a cathode;
   an anode; and
   an electrolyte according to claim 3.

10. The device of claim 9, wherein the cathode comprises a lithium metal oxide, spinel, olivine, carbon-coated olivine, vanadium oxide, lithium peroxide, sulfur, polysulfide, a lithium carbon monofluoride or mixtures of any two or more thereof.

11. The device of claim 10, wherein the lithium metal oxide is $LiCoO_2$, $LiNiO_2$, $LiNi_xCo_yMet_zO_2$, $LiMn_{0.5}Ni_{0.5}O_2$, $LiMn_{0.3}Co_{0.3}Ni_{0.3}O_2$, $LiMn_2O_4$, $LiFeO_2$, $Li_{1+x'}Ni_\alpha Mn_\beta Co_\gamma Met'_\delta O_{2-z'}F_{z'}$, where Met is Al, Mg, Ti, B, Ga, Si, Mn or Co; Met' is Mg, Zn, Al, Ga, B, Zr or Ti; and wherein $0 \leq x \leq 0.3$, $0 \leq y \leq 0.5$, $0 \leq z \leq 0.5$, $0 \leq x' \leq 0.4$, $0 \leq \alpha \leq 1$, $0 \leq \beta \leq 1$, $0 \leq \gamma \leq 1$, $0 \leq \delta \leq 0.4$, and $0 \leq z' \leq 0.4$.

12. The device of claim 9, wherein the anode comprises lithium metal, graphitic material, amorphous carbon, $Li_4Ti_5O_{12}$, tin alloy, silicon alloy, intermetallic compound or mixtures thereof.

13. The device of claim 9, wherein the device comprises a lithium battery, lithium-ion battery, lithium-sulfur battery, lithium-air battery, sodium ion battery, magnesium battery, lithium/$MnO_2$ battery, or Li/poly(carbon monofluoride) battery.

14. The device of claim 9, further comprising a porous separator separating the anode and cathode from each other.

15. The device of claim 14, wherein the porous separator comprises an electron beam-treated micro-porous polyolefin separator or a microporous polymer film comprising nylon, cellulose, nitrocellulose, polysulfone, polyacrylonitrile, polyvinylidene fluoride, polypropylene, polyethylene, polybutene, or co-polymers or blends of any two or more such polymers.

16. The device of claim 9, wherein the device comprises a capacitor or solar cell.

17. The device of claim 9, wherein the cathode is $LiFePO_4$ or $A_nB_2(XO_4)_3$, where A is Li, Ag, Cu, Na, Mn, Fe, Co, Ni, Cu or Zn; B is Ti, V, Cr, Fe or Zr; X is P, S, Si, W or Mo and wherein $0 \leq n' \leq 3$.

18. The electrolyte of claim 3, wherein the metal salt is an alkali metal salt.

19. The electrolyte of claim 18, wherein the cation of the alkali metal salt comprises lithium or sodium.

20. The electrolyte of claim 3, wherein the metal salt is an aluminum salt or a magnesium salt.

21. The compound of claim 1, wherein the aryl is phenyl or benzyl.

22. The compound of claim 1, wherein $Q^+$ is pyrrolidinium, piperdinium, imidazolium, or pyridine.

23. The compound of claim 1, wherein $R_1$ and $R_2$ are independently a silane.

24. The compound of claim 1, wherein X is phenylene.

* * * * *